(12) United States Patent
Lawitschka et al.

(10) Patent No.: US 9,330,205 B2
(45) Date of Patent: May 3, 2016

(54) COMPUTER-IMPLEMENTED METHOD FOR DIGITALLY DESIGNING A DENTAL RESTORATION AND A COMPUTER-READABLE MEDIUM

(75) Inventors: Uwe Lawitschka, Berlin (DE); Marcus Meier, Basel (CH); Martin Manzer, Berlin (DE); Melanie Welge, Gräfelfing (DE)

(73) Assignee: Straumann Holding AG, Basel (CH)

( * ) Notice: Subject to any disclaimer, the term of this patent is extended or adjusted under 35 U.S.C. 154(b) by 495 days.

(21) Appl. No.: 13/812,093

(22) PCT Filed: Aug. 23, 2011

(86) PCT No.: PCT/EP2011/004231
§ 371 (c)(1),
(2), (4) Date: Mar. 21, 2013

(87) PCT Pub. No.: WO2012/028271
PCT Pub. Date: Mar. 8, 2012

(65) Prior Publication Data
US 2013/0185027 A1    Jul. 18, 2013

(30) Foreign Application Priority Data

Aug. 31, 2010  (EP) ..................... 10009046
Aug. 31, 2010  (EP) ..................... 10009047
Mar. 18, 2011  (EP) ..................... 11002250

(51) Int. Cl.
*G06F 17/50*    (2006.01)
*A61C 13/00*    (2006.01)
*A61C 5/10*    (2006.01)

(52) U.S. Cl.
CPC . *G06F 17/50* (2013.01); *A61C 5/10* (2013.01); *A61C 13/0004* (2013.01)

(58) Field of Classification Search
CPC ....... A61C 13/0004; A61C 5/10; G06F 17/50
USPC .......................... 703/1; 433/24; 700/98, 118
See application file for complete search history.

(56) References Cited

U.S. PATENT DOCUMENTS

2009/0246726 A1    10/2009  Chelnokov et al.

OTHER PUBLICATIONS

Tao et al., "Computer Aided Design and Deformation of the Complete Crown", May 16-18, 2008, The 2nd International Conference on Bioinformatics and Biomedical Engineering ICBBE, pp. 1699-1702.*

(Continued)

*Primary Examiner* — Kamini S Shah
*Assistant Examiner* — Juan Ochoa
(74) *Attorney, Agent, or Firm* — Therese A. Hendricks, Esq.

(57) ABSTRACT

Computer-implemented method for digitally designing a dental restoration for a rest tooth, wherein the rest tooth is described by data of the rest tooth and wherein a tooth template is described by data of the tooth template, by means of an Laplacian surface deformation to deform the tooth template towards the surface of the rest tooth, wherein the method uses, for the Laplacian surface deformation, an angle weighting function depending on: the angle between the normal direction of a target on the surface of the rest tooth or the normal direction of a handle on the tooth template; and the direction of a line connecting the target and the handle; wherein the angle weighting function is used to weight the handle for deforming the tooth template towards the rest tooth. Further, the invention is related to a computer-readable medium having stored thereon instructions, which when executed by a processor, are adapted to perform the method steps of the inventive computer-implemented method.

12 Claims, 7 Drawing Sheets

(56) References Cited

OTHER PUBLICATIONS

Tao et al., "Digital Design of Fixed Bridge Framework", May 16-18, 2008, 2nd International Conference on Bioinformatics and Biomedical Engineering, ICBBE, pp. 1792-1795.*

Stoll et al., "A Volumetric Approach to Interactive Shape Editing", Jun. 2007, MPI-I-2007-4-004, pp. 1-23.*

Botsch et al., On Linear Variational Surface Deformation Methods, 2008, IEEE Transactions on Visualization and Computer Graphics, vol. 14, Issue 1, pp. 213-230.*

Nealen et al., Laplacian mesh optimization, 2006, GRAPHITE '06 Proceedings of the 4th international conference on Computer graphics and interactive techniques in Australasia and Southeast Asia, pp. 381-389.*

Yuan et al., "Single-tooth modeling for 3D dental model", 2010, International Journal of Biomedical Imaging vol. 2010, Article ID 535329, pp. 1-14.*

3.1 Tangent plane and surface normal—MIT, Dec. 2009, pp. 1-4.*

Steinbrecher T. "Dental Inlay and Onlay Construction by Iterative Laplacian Surface Editing", Computer Graphics Forum Jul. 2008, Blackwell Publishing LTD GB, Eurographics Symposium on Geometry Processing 2008, Pierre Alliez and Szymon Rusinkiewicz, vol. 27 (2008), No. 5, pp. 1441-1447.

European Search Report mailed Jan. 13, 2011 in application EP 10 00 9046.

European Search Report mailed Mar. 24, 2011 in application EP 10 00 9047.

European Search Report mailed Dec. 2, 2011 in application EP 11 00 2250.

European Search Report mailed Aug. 29, 2012 in application EP 12 00 1137.

International Search Report mailed Dec. 12, 2011 in PCT/EP2011/004232.

International Search Report mailed May 3, 2012 in PCT/EP2011/004230.

International Search Report mailed Feb. 13, 2012 in PCT/EP2011/004231.

International Search Report mailed Feb. 13, 2012 and Preliminary Report on Patentability in corresponding PCT/EP2011/004231 mailed Mar. 14, 2013.

Steinbrecher T. et al., "Dental inlay and onlay construction by iterative laplacian surface editing". Computer Graphics Forum Jul. 2008, Blackwell Publishing Ltd. GB, vol. 27, No. 5, Jul. 2008, pp. 1441-1447, XP002616277.

* cited by examiner

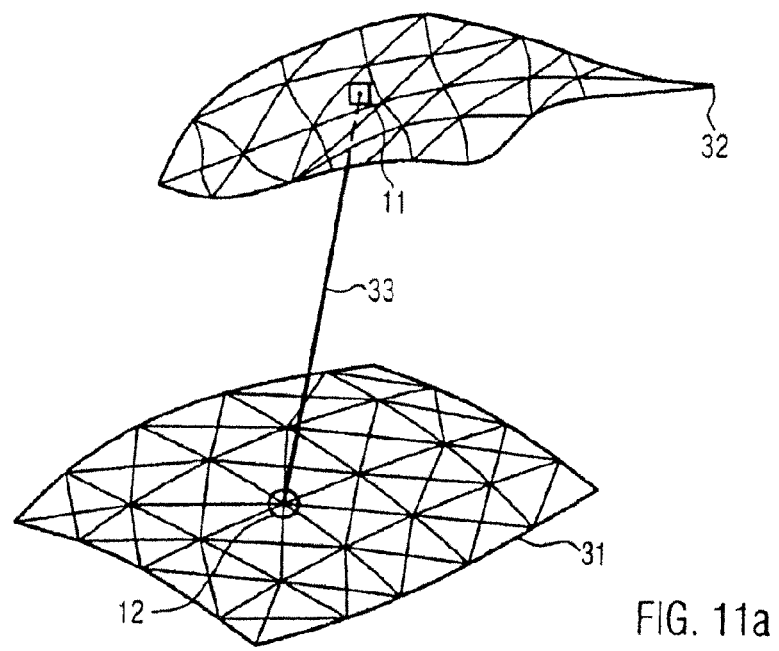
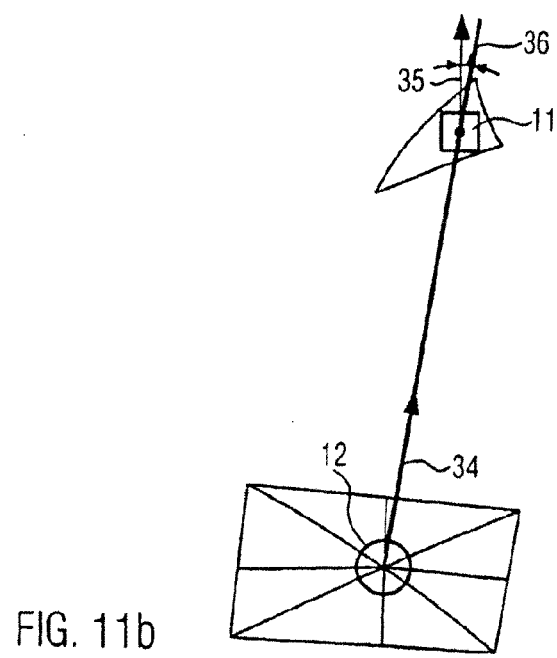
FIG. 11a
FIG. 11b automatically deforming the tooth template towards the surface of the rest tooth by Laplacian surface deformation using an angle weighing function depending on:

the angle between the normal direction of a target on the surface of the rest tooth or the normal direction of a handle on the tooth template; and the direction of a line connecting the target and the handle;

wherein the angle weighting function is used to weight the handle for deforming the tooth template towards the rest tooth

FIG. 12

COMPUTER-IMPLEMENTED METHOD FOR DIGITALLY DESIGNING A DENTAL RESTORATION AND A COMPUTER-READABLE MEDIUM

FIELD OF THE INVENTION

The invention relates to a computer-implemented method for digitally designing a dental restoration and to a computer-readable medium.

BACKGROUND

The design of tooth restorations requires a deep dental knowledge. The challenge of computer aided tooth design lies in the computation of a functional correct morphology of the missing chewing surface. A solution must be robust and automated such that the user actually benefits from time saving and better results.

The article "Dental inlay and onlay construction by iterative Laplacian surface editing" by T. Steinbrecher et al. (Eurographics Symposium on Geometry Processing 2008; July 2-4, 2008 in Copenhagen, Denmark; Volume 27(2008), No. 5; p. 1441-1447) discloses that a model tooth may be adapted by using Laplacian surface editing to a patient's tooth. After adaptation, the part of the model tooth lying above the cavity will be joined with the cavity mesh to create the actual inlay reconstruction. The part of the model tooth lying above the healthy part of the tooth should be adapted to the remaining tooth surface. The model tooth is segmented into parts that lie "above cavity" or "on surface".

From each vertex of the model tooth that is not yet clarified as "above cavity", two rays are cast, one towards the centre of the tooth to be reconstructed, and one away from it. Thereby all rays by definition pass through the centre of the tooth to be reconstructed. Only the closest hit point is considered. The hit points are then classified according to their location as "above cavity", "on surface", or "undefined".

The adaptation is an iterative process, alternating segmentation and deformation. For vertices classified as "on surface", ray collisions with the tooth to be reconstructed are used again.

As the rays are cast, for each iteration, starting from a vertex of the model tooth also the segmentation has to be performed again. This is because by starting from a vertex of the model tooth, it is unknown where the location of a hit point on the tooth to be reconstructed will be. Even before the first deformation of the model tooth it needs to be segmented.

Desired deformation vectors may be weighted by deformation weights and further a global deformation weight linearly depending on the iteration step may be used as a scaling factor for all weights.

After the adaptation is completed, all vertices classified as "on surface" and not having a neighbor that is classified as "above cavity" will be removed and thus a mesh that covers the cavity remains wherein its boundary is aligned to the preparation margin.

SUMMARY OF THE INVENTION

It is the object of the present invention to enable an automatic design of dental restorations by means of Laplacian surface deformation resulting in stable and reliable data for a dental restoration.

All the method steps described in the following may be performed automatically and do not necessarily need the interaction of a user.

The present invention relates to a computer-implemented method for digitally designing a dental restoration for a rest tooth, wherein the rest tooth is described by data of the rest tooth and wherein a tooth template is described by data of the tooth template, by means of an Laplacian surface deformation to deform the tooth template towards the surface of the rest tooth, wherein the method uses, for the Laplacian surface deformation, an angle weighting function depending on:

the angle between the normal direction of a target on the surface of the rest tooth or the normal direction of a handle on the tooth template; and the direction of a line connecting the target and the handle;

wherein the angle weighting function is used to weight the handle for deforming the tooth template towards the rest tooth.

A rest tooth may be considered as a tooth of a patient and/or (digital) data describing it, wherein said tooth is not complete, i.e. has missing parts, due to caries, dental preparation like milling and so on. For the processes in the computer-implemented method digital data of the rest tooth may be used, wherein these data may be achieved by scanning of a dental model of the rest tooth or by directly scanning the patient's rest tooth. The surface of the rest tooth may be described by a mesh of triangles, wherein the triangles may all be the same or wherein the triangles may have different shapes. It is also possible to use other polygons and/or use different polygons (e.g. like triangles and pentagons) in one mesh.

The rest tooth may have a prepared surface/prepared part which in general means that this surface/part has been prepared, e.g. by a dentist by milling. Preferably, the prepared surface/part may be provided with a dental restoration. Further, the rest tooth may have an unprepared surface/unprepared part at which the intact surface of the rest tooth is present. In some cases a non-intact surface of the rest tooth may be considered as "unprepared", e.g. in case no dental restoration should or will be provided to this surface of the rest tooth.

A tooth template may represent a digital representation of a generic tooth, wherein tooth templates according to the different tooth types (molar, premolar, incisor etc.) may be provided. The surface of the tooth template may be described by a mesh of triangles, wherein the triangles may all be the same or wherein the triangles may have different shapes. It is also possible to use other polygons and/or use different polygons (e.g. like triangles and pentagons) in one mesh.

By taking into account also an angle weighting function for performing a Laplacian surface deformation to deform a tooth template towards a rest tooth, an advanced digital design of a dental restoration is enabled, as the shapes of the rest tooth and/or tooth template may directly be taken into account by the normal direction of the target and/or the normal direction of the tooth template. Thereby for example good pairs of a target and a handle can be indentified. In case the angle between the normal direction and the line connecting the target and the handle is small, the target and the handle may be considered to fit together such that a high weight for the target (or the pair of handle and target) may be assigned for deformation. If the connecting line has a large angle with the normal direction, this can be seen as an indication that the handle and the target do not fit together very well. Hence in the deformation the handle (or the pair of handle and target) can be assigned a low weight. Other considerations of the angle are possible as well.

The method may further comprise defining the line connecting the target and the handle as being directed along the normal direction of the target or along the normal direction of the handle.

In this case, the angle indicates the deviation between the normal direction of the handle and the normal direction of the target. Thus, the angle may be considered to be a measure how similar the shapes of the rest tooth and the tooth template are. The smaller the angle the better is the similarity between the shapes.

The method may further comprise defining the angle weighting function as decreasing with increasing angle. For small angles the shapes the rest tooth and the tooth template may be assumed similar and therefore, higher weights may be used for them as compared to angles with larger values. For angles with larger values, it may be assumed that a larger difference in the shapes of the rest tooth and the tooth template are present as also the difference in the normal directions of the target and of the handle are larger.

The decrease of the angle weighting function may for example be described by a Wendland weighting function.

The method may use a product of the angle weighting function and at least one or two of a global weighting function or a distance weighting function to weight the handle for deforming the tooth template towards the rest tooth. By using a product of two or three weighting functions representing different dependencies, e.g. of angle, iteration step and/or distance, the deformation of the tooth template may be improved as the deformation of the handles may be performed taking into account various aspects.

The method may further comprise defining the global weighting function as increasing with each iteration step in case the Laplacian surface deformation is performed iteratively.

Further the distance weighting function may be defined as decreasing with increasing distances between the target and the handle, wherein the dependence of the distance weight on the distance may vary with each iteration step in case the Laplacian surface deformation is performed iteratively.

In order to allow for a general position of the template, weights may be independent from the distance at the beginning of the iteration process. As the iteration proceeds large distances may be penalized more and more by reducing the respective handle weights.

This may reduce the impact of false projections. The less the distance, the more certain it may be that a correct projection is found.

The method may further comprise defining the data of the tooth template as a first polygonal mesh describing the surface of the tooth template and defining the data of the rest tooth as a second polygonal mesh describing the surface of the rest tooth, wherein the handle lies inside a polygon of the first mesh, on an edge of a polygon of the first mesh or on a vertex of a polygon of the first and/or wherein the target lies inside a polygon of the second mesh, on an edge of a polygon of the second mesh or on a vertex of a polygon of the second mesh.

The method may further comprise defining the normal direction of the target/handle for example by one of the three following possibilities:
- when the target/handle lies within the polygon, by the normal direction of the polygon of the second/first mesh or by an average of the normal direction of the polygon and the normal directions of its neighboring polygons or of polygons that lie within a sphere or a volume of a predefined size (and/or shape) around the polygon;
- when the target/handle lies on an edge of a polygon of the second/first mesh, by the average of the normal directions of polygons having this edge, or the average of normal directions of these polygons and their neighboring polygons or the average of normal directions of polygons that lie within a sphere or a volume of a predefined size (and/or shape) around the vertex;
- when the target/handle lies on a vertex (a corner of a polygon) of a polygon of the second/first mesh, by an average of the normal directions of polygons that have this vertex as a corner point (or additionally their neighboring polygons) or of polygons that lie within a sphere or a volume of a predefined size (and/or shape) around the vertex.

The average of the normal directions may be a weighted average wherein the weight may depend on the size of a triangle or it may be an unweighted average where all triangles considered for averaging are taken into account with equal weights.

In general, a normal direction to a surface at a point is typically the same as the normal direction to the tangent plane to said surface at said point.

For the targets and for the handles any point of a surface can be used. This means that a point on a surface of the rest tooth or a point on the template can be either a point inside a triangle (or polygon in general) or may be a corner of a triangle (or polygon in general) in case the surface of the rest tooth and the template are described by a mesh comprising triangles (or polygons in general). This on the one hand gives more flexibility in the choice of targets and handles as compared to the prior art but additionally allows for triangles (or polygons in general) of largely different sizes to be used. There is no need to have a large number of relatively small triangles in order to describe the surface of the rest tooth or the tooth template which assures that there is a sufficiently high density of vertices in order to perform a reasonable surface deformation. Since in the present method also points inside a triangle may be used there is no need for a large number of vertices and triangles of largely different size may be used. E.g. triangles having a two dimensional size of their surface 10 times or 50 times the two dimensional size of the surface of the smallest triangle of the data set can be used. This allows for reduced data sets for the digital description of the surface of the rest tooth and of the template in comparison to the prior art.

All vertices of a portion of a mesh describing the rest tooth portion that is considered for the Laplacian deformation can be used as targets or only a portion (subset thereof). Also at least one point of each triangle (polygon) of a mesh describing the rest tooth portion that is considered for the Laplacian deformation can be used as targets or only a portion (subset) of the triangles.

Moreover, automatically deforming the tooth template in the Laplacian surface deformation towards the rest tooth may further comprise moving the handle towards the target.

Using a handle that lies in a direction normal to the surface at the point of the target or a target that lies in a direction normal to the surface at the point of the handle additionally contributes to robust and reliable results using the Laplace surface deformation. By having handles and targets aligned in a direction normal either to the surface of the rest tooth or normal to the surface of the tooth template a good choice of a handle and a corresponding target is found which allows for deformation of a template into a proper tooth surface.

It is possible to first define a target on the surface of the rest tooth and then to identify the corresponding handle in a direction normal to the surface of the rest tooth. Thus a target may be provided at specific points of the surface of the rest tooth which may be of particular interest. Such a point may e.g. be on the preparation margin. By firstly choosing the target on the surface of the rest tooth and then choosing a corresponding handle it may thus be assured that a point of particular importance may be taken into account for the surface deformation. If first the handles are defined and afterwards the corresponding targets are chosen, then it cannot be assured that specific points of the surface of the rest tooth which are of particular interest are taken into account. The preparation margin defines the border line of the prepared surface and the unprepared surface of the rest tooth that should be provided with a dental restoration. Taking points of the preparation margin into account for the surface deformation may result in a smooth transition at the preparation margin, i.e. a smooth transition between the dental restoration and the rest tooth at the preparation margin.

Iteratively performing the deformation of the tooth template may use a handle weight that is increased as the iteration process proceeds, preferably starting with a pre-defined minimum handle weight.

By iteratively increasing the weight, the general position of the tooth template may be is first adjusted to the outer surface of the rest tooth, thus the shape preservation may be predominant and self-intersection may be avoided. As the iteration proceeds and weights increase, the method may find correct handles and the template may be more and more deformed towards the surface of the rest tooth.

The method may further comprise the step of defining the handle weight for the deformation step as a product comprising a global weight increasing with each iteration step, and at least one or two of a distance weight decreasing with increasing distances between the target and the handle, wherein the dependence of the distance weight on the distance may vary with each iteration step, or an angle weight that depends on the angle between the normal direction of the target and the normal direction of the handle.

A result of the inventive method may be that the transition between the rest tooth and the tooth template is as smooth as possible, which means that sharp edges and transitions which may achieve high loads are prevented.

The method may further comprise the step of automatically extracting a portion of the tooth template by digitally cutting the deformed tooth template along a preparation margin.

For designing the dental restoration, it may be sufficient to use the deformed tooth template that is located within the preparation margin as this is the area that should be provided with the dental restoration in order to achieve a complete tooth structure.

Moreover, the method may comprise the step of combining data representing the cut out deformed tooth template portion with data representing the surface of the rest tooth inside the preparation margin to provide a three-dimensional design of the dental restoration.

The surface of the rest tooth may have been scanned in order to get a corresponding data set. The rest tooth may comprise prepared regions, i.e. regions where original tooth material is missing either by medical defects and/or milling. The preparation margin defines the border line between prepared regions of the rest tooth and regions in which the rest tooth has its original shape. Thus, for the definition and thus also for the design of a complete dental restoration both the cut out deformed tooth template and the surface of the rest tooth inside the preparation margin have to be known in order to define and thus may be able to design the shape of the dental restoration.

Further, a cement gap and/or a spacer gap may be added to the data representing the surface of the dental restoration that would be in contact with or facing towards the rest tooth, the so-called lower surface.

The cement gap may be filled with dental cement or the like in order to fix a physical dental restoration to a rest tooth of a patient. This gap may be provided between the dental restoration and the surface of the rest tooth by providing a dental restoration with dimensions smaller than the space available at the rest tooth. The thickness of the cement gap may be between 10 and 60 µm, or may be smaller or thicker, e.g. depending on the grain size of the dental cement and/or the thickness of the dental restoration.

The spacer gap may be provided in addition to the cement gap (or alone), e.g. to provide a broadening of the cement gap at positions away from the preparation margin, e.g. to increase the amount of cement that may be used for fixing the dental restoration.

The adding may be performed by applying an offset along the normal directions of points on the lower surface, such as vertices, wherein preferably the normal directions may be averaged about a defined region around each point.

A cement gap may be required to provide space for the cement that is needed to securely attach a physical dental restoration to a rest tooth of a patient. An additional spacer gap may be provided. Next to the preparation margin only the cement gap may be provided and at a first predefined distance to the preparation margin a smooth transition from the cement gap to the spacer gap may be provided, reaching some pre-defined spacer gap thickness at a second predefined distance from the preparation margin.

The surface of the dental restoration may be further adapted according to a cutter radius (e.g. of a milling tool) that will be used for preparing the physical dental restoration.

An adaptation to the cutter radius may be needed to ensure that the manufactured dental restoration fits to the rest tooth and to ensure that the dental restoration may be manufactured with all its required details. For example, when the cutter radius has a dimension that is larger than a structure that the dental restoration to be manufactured should have this structure would have to be adapted, i.e. the structure must be designed to have a size corresponding to the cutter radius.

The method may further comprise the step of determining whether the dental restoration has a pre-defined minimum thickness, wherein the minimum pre-defined thickness may have different or equal values in different regions of the dental restoration, preferably by determining whether the vertices of the cut out deformed tooth template have a pre-determined distance to the lower surface, wherein the pre-defined distance may have different or equal values in different regions of the dental restoration.

One possibility to determine whether the dental restoration would have a pre-defined minimum thickness is defining a volume on the prepared part of the rest tooth, the surface of the volume not being in contact with the prepared part of the rest tooth and describing a so-called minimal surface which may define the minimum wall thickness the dental restoration may have.

The method may further comprise the step of moving vertices of the cut out deformed tooth template that lie inside the volume to the surface of the volume not being in contact with the prepared part of the rest tooth by means of the Laplacian surface deformation.

For a computer-aided manufacturing of the dental restoration or any other manufacturing process the dental restoration may have to have a predefined minimal wall thickness to ensure that the dental restoration will not break or will not be damaged in some way during the manufacturing process and/or when being attached to a rest tooth and/or during daily use in the attached state.

For this Laplacian surface deformation (to ensure a minimal thickness), a handle weight may be defined wherein no iteration depending weight is needed as no general positioning is required in case of adapting the dental restoration to provide a minimum wall thickness.

During this Laplacian surface deformation, first the deformation may be applied to the boundary of the deformed tooth template while fixing handles in the interior of the deformed tooth template, and then in a second step the deformation may be applied to the interior while fixing handles on the boundary. The boundary of the deformed tooth template may be defined by the circumferential border of the surface.

These two subsequent processes ensure that the Laplacian surface deformation does not move the deformed tooth template out of the minimal surface.

The method may further comprise the step of positioning the tooth template, which preferably may be selected from a data base comprising one or more tooth templates for one or more tooth types, with respect to rest tooth by aligning the rest tooth and the tooth template to coincide in x direction and in z direction.

Both the coordinate systems of the rest tooth and the tooth template may have the x direction in buccal (vestibular) direction, the y direction along the mesial-distal axis and the z direction in occlusal direction.

The position of the tooth template may be adjusted to a maximum z value that may be defined by a highest extend of one or more neighboring teeth. A plane may be drafted perpendicular to the occlusal axis of said rest tooth and its maximum value of height of the rest tooth of any of the neighboring tooth. Then the tooth template may be adjusted such that it has at least one common point with this plane but does not intersect the plane. In case no neighboring tooth or teeth is or are present the plane may be provided at a z value which may be offset by predefined value from the top value of the rest tooth.

Moreover, the tooth template may be scaled to x and y direction according to the horizontal extent of the prepared surface of the rest tooth, wherein preferably no scaling in z direction is performed.

Due to the local coordinate systems of rest tooth and tooth template, the translation of the tooth template to adjust it to a defined height and the scaling in buccal direction, an automated positioning of the tooth template (prior to the Laplace surface deformation) may be achieved.

A further aspect may be given by a computer-implemented method for digitally designing a dental restoration for a rest tooth, wherein the rest tooth is described by data of the rest tooth and wherein a tooth template is described by data of the tooth template, the method comprising the step of automatically deforming the tooth template by means of Laplacian surface deformation such that a prepared part of the rest tooth is covered (matched) by a portion of the tooth template wherein the data describing the tooth template define a mesh comprising polygons, such as triangles and one or more handles for the Laplacian surface deformation are provided inside of the polygon.

By having one or more handles provided inside of a polygon, such as a triangle, there is no need for a dense set of small triangles as explained above.

According to another aspect there may be provided a computer-implemented method for digitally designing a dental restoration for a rest tooth, wherein the rest tooth is described by data of the rest tooth and wherein a tooth template is described by data of the tooth template, the method comprising the step of automatically deforming the tooth template by means of Laplacian surface deformation such that a prepared part of the rest tooth is covered by a portion of the tooth template wherein firstly a point on the surface of the rest tooth is chosen as a target of the Laplacian surface deformation and then based on the chosen target a point on the tooth template is chosen as a handle.

Such a method may have as a result that specific points, such as points on the preparation margin, are used for defining a target (as explained above) and that no new and separate segmentation of the template is necessary as the target points do not change from iteration to iteration.

In a further aspect there is provided a computer-implemented method for digitally modifying a dental restoration for a rest tooth, wherein the dental restoration is described by data of the dental restoration, the method comprising the step of:

automatically deforming the dental restoration by means of Laplacian surface deformation such that the thickness thereof is increased up to a predefined minimum thickness of the dental restoration.

Thereby it is made sure that the dental restoration has a minimum thickness, which makes sure that the dental restoration can be manufactured without significant problems and also makes sure that the dental restoration does not break in use due to a to small thickness. At the same time the digital deformation of the dental restoration by the Laplacian surface deformation leads to smooth surfaces without kinks or sharp bends. Details of this Laplacian surface deformation are disclosed above in and in relation to FIG. 6.

Further, the present invention is related to a computer-readable medium having stored thereon instructions, which when executed by a processor, are adapted to perform any of the above identified method steps.

BRIEF DESCRIPTION OF THE DRAWINGS

Preferred embodiments of the invention will be illustrated with reference to the enclosed figures. In the figures:

FIG. 11*a* shows the distance between a target on the rest tooth and a handle on the tooth template; and FIG. 11*b* shows an enhanced view of FIG. 11*a*.

FIG. 12 is a flow chart of a method according to one embodiment of the invention.

DETAILED DESCRIPTION

The schematic representations shown in FIGS. 1 to 11*b* may be displayed for example on a computer display or the like, wherein data sets may be provided corresponding to the depicted objects.

Figure 1:
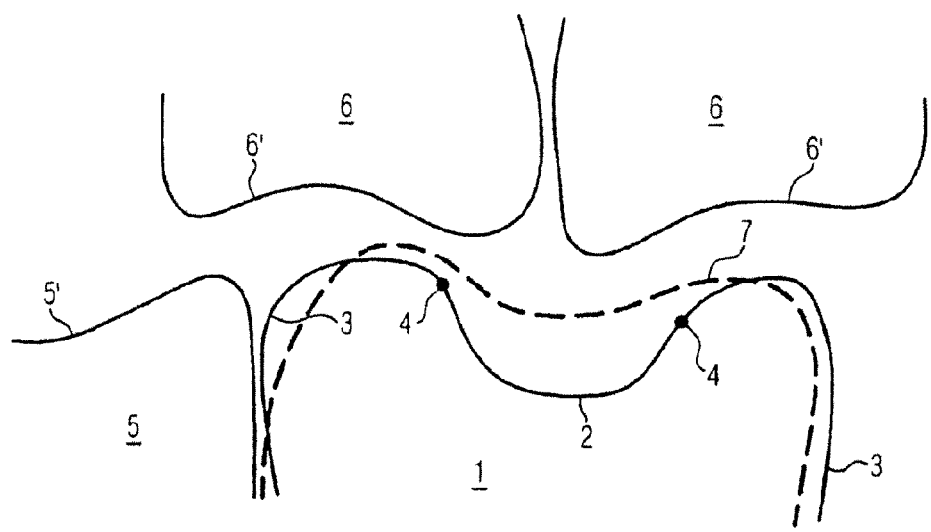
FIG. 1 shows a prepared tooth with surrounding teeth and a tooth template.

FIG. 1 shows schematically a rest tooth 1 comprising a prepared region, the so-called lower surface 2, which is separated from the unprepared rest tooth, the so-called outer surface 3, by the preparation margin 4. The depicted rest tooth 1 has a neighboring tooth 5 with an approximal surface 5' and two opposite teeth 6 with occlusal surfaces 6'. In order to provide the rest tooth 1 with a dental restoration a tooth template 7 may be to used. The tooth template 7 may be positioned with respect to the rest tooth 1 such that the local coordinate systems of the rest tooth 1 and the tooth template 7 coincide in x direction and in z direction. For example, the x direction may be given by the buccal direction, the y direction by the mesial-distal axis and the z direction by the occlusal direction.

The rest tooth 1 shown in FIG. 1 comprises a cavity as prepared region, which means that the dental restoration to be designed may be an inlay. However, a rest tooth may also have prepared regions extending on surface regions, such as one or more cusp tips which means that the dental restoration to be designed may be an onlay or partial crown. A veneer may have to be designed when a thin layer of the tooth surface has to be provided with a dental restoration.

Figure 2:
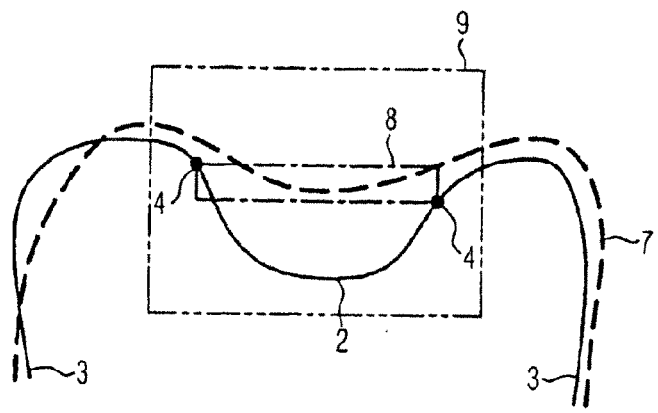
FIG. 2 shows a prepared tooth, a tooth template, first and second bounding boxes.

As shown in FIG. 2, for performing the deformation of the tooth template 7 a first bounding box 8 may be defined by the preparation margin 4, A second bounding box 9 may be defined in a predefined distance from the first bounding box 8 such that part of the tooth template 7 and part of the outer surface 3 of the rest tooth 1 are cut out. By using the second bounding box 9 the deformation process may be simplified and accelerated as not the whole tooth template 7 will be deformed but only the part of it which is located within the second bounding box 9. A predefined distance to the first bounding box 8 may be kept in order to avoid cut out fissures in the tooth template 7. However, for performing the deformation of the tooth template 7, the use of bounding boxes is not necessarily required.

Figure 3:
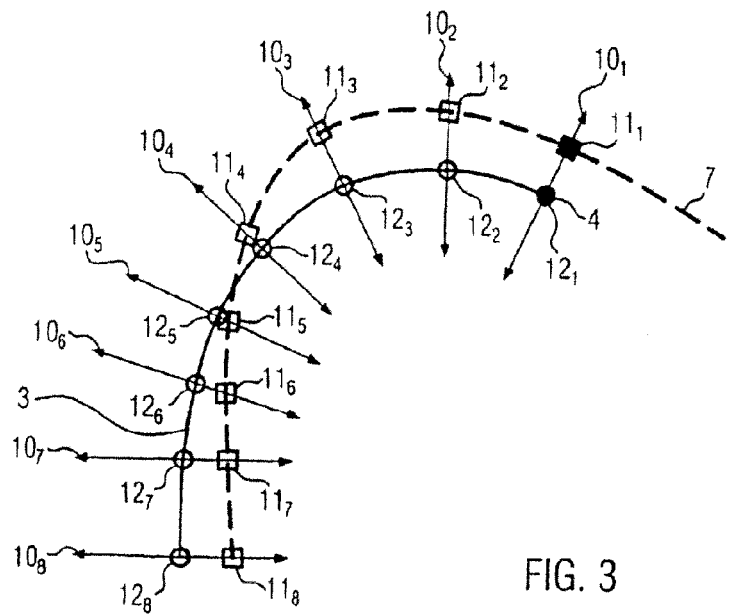
FIG. 3 shows rays to select handles and targets.

For deforming the tooth template 7 such that the cavity in the rest tooth 1 may be covered by a suitable part of the tooth template 7, an algorithm may be used, wherein as shown in FIG. 3, lines 10₁-10₈ are cast each going through a point on the surface of the rest tooth, each of the lines being directed along the normal direction of the point of the surface of the rest tooth. The lines may be cast starting at points on the outer surface 3 of the rest tooth 1 or starting at points on the preparation margin 4.

If an intersection of a line 10₁-10₈ with the tooth template 7 is observed the respective intersection point on the template 7 may be chosen as handle 11₁-11₈ (squares) and the respective point on the rest tooth 1 as respective target 12₁-12₈ (circles). If an intersection of a line 10₁-10₈ with the tooth template 7 is observed in both positive and negative normal directions, the intersection point with the smaller distance to the point the line going through of the surface of the rest tooth 1 may be chosen.

The open circles 12₂-12₈ correspond to targets on the outer surface 3 of the rest tooth 1 having respective handles on the tooth template 7 indicated by the open squares 11₂-11₈. The filled circle 12₁ corresponds to a point on the preparation margin 4 and the respective handle on the tooth template 7 is indicated by the filled square 11₁.

Other methods for defining targets and handles are possible as well.

After having determined the handles 11₁-11₈ on the tooth template 7 and respective targets 12₁-12₈ on the rest tooth 1, the deformation of the tooth template 7 may be performed as an iterative process.

The deformation of the tooth template 7, according to the targets 12₁-12₈ may be performed in the unprepared region of the rest tooth 1 and at the preparation margin 4. As the algorithm starts at points on the surface of the rest tooth 1 and the algorithm uses these points as targets 12₁-12₈, it is not required to make a determination after each iteration step whether a point of the tooth template 7 which may be a handle for the next iteration step lies above the prepared or the unprepared region of the rest tooth 1 or above the preparation margin 4. The algorithm may be considered to deform the tooth template 7 by pulling the tooth template 7 towards the rest tooth 1 and as the location of the targets 12₁-12₈ on the rest tooth 1 is known, it is also known that a handle on the tooth template 7 will be deformed towards this location.

Figure 4A:
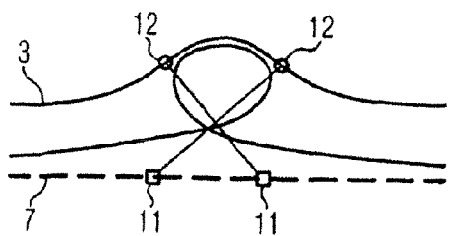
FIG. 4*a* shows the result of a surface deformation in a single step.
Figure 4B:
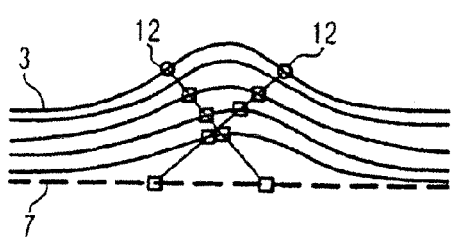
FIG. 4*b* shows the result of a surface deformation using an iterative process with successively increasing handle weights.

Handle weights may increase from low values to bigger values successively during the iterative process. FIGS. 4a and 4b illustratively show the result when performing the deformation in a single step and when performing the deformation using an iterative process, respectively. When using a single step for performing the deformation, self-intersections may be produced resulting in a deformed surface that is not usable for a dental restoration. However, when the iteration starts with low handle weights, the shape preservation characteristic of the Laplacian surface deformation is predominant and self-intersection is avoided. As shown in FIG. 4b the deformed tooth template 7 is adjusted to fit the outer surface 3.

Once new handles are selected, the new deformed shape of the tooth template has to be calculated. This may be achieved by solving an optimization problem, wherein a global deformation energy E may be constructed that measures how much a deformed triangle mesh with vertex coordinates $p_1', \ldots, p_n'$ differs from its initial rest pose with vertex coordinates $p_1, \ldots, p_n$. The deformation energy E integrates locally defined changes of the shape. The local shape of vertex i is described by the discrete Laplacian $\Delta p_i = 2H_i n_i$ which is a three dimensional vector that points in the direction of the unit length vertex normal $n_i$ and has a magnitude twice the mean curvature $H_i$.

The global deformation energy may be formulated as $$E(p_1', \ldots p_n') = \sum_i A_i \|\delta_i' - \delta_i\|^2 + \sum_j w_j \|h_j' - h_j\|^2, \quad (1)$$

wherein the left term measures the weighted squared distance between local shapes in the deformed mesh and local shapes in the rest pose. The right term of equation 1 measures the weighted squared distance between the positions of the deformed handles $h_j' = h_j(p'1, \ldots, p'n)$ and their targets $h_j = h_j(p_1, \ldots, p_n)$. $A_i$ is the two dimensional Voroni area around the vertex i and $w_j = 1$.

The discrete Laplacian may be computed as $$\delta_i = \frac{1}{2 \cdot A_i} \cdot \sum (\cot \alpha_{ij} + \cot \beta_{ij}) \cdot (p_i - p_j), \quad (2)$$

wherein vertices j are the one-ring neighbours of vertex i and $\alpha_{ij}$ and $\beta_{ij}$ are the two angles opposite to the edge (i,j). In the presence of obtuse triangles, the respective Voroni region extends beyond the one-ring neighbours of the vertex. To guarantee a perfect tiling of the surface without overlapping the Voroni area is truncated, resulting in the Laplacian of a deformed vertex being:

$$\delta_i' = \frac{1}{2 \cdot A_i'} \cdot \sum (\cot \alpha_{ij}' + \cot \beta_{ij}') \cdot (p_i' - p_j'), \quad (3)$$

The handles j are allowed to be at any point of the triangle surface (and not only being vertices) by using barycentric coordinates $(\lambda_{j1}, \lambda_{j2}, \lambda_{j3})$ of the respective triangle $(p_{j1}, p_{j2}, p_{j3})$:

$$h_j(p_1, \ldots, p_n) = \lambda_{j1} p_{j1} + \lambda_{j2} p_{j2} + \lambda_{j3} p_{j3}, \quad (4)$$

where $$\lambda_{jk} = \frac{\|(p_{ja} - h_j) \times (p_{jb} - h_j)\|}{\|(p_{j2} - p_{j1}) \times (p_{j3} - p_{j1})\|} \quad (5)$$

for $a \neq b$, $a \neq k$ and $b \neq k$.

It is assumed that areas and angles are preserved such that $\alpha'_{ij} = \alpha_{ij}$, $\beta'_{ij} = \beta_{ij}$ and $A'_i = A_i$, and hence, the Laplacian operator $\Delta p'_i$ can be described linearly in the deformed vertex coordinates. Thus, the global deformation energy E has a quadratic form $$E(p') = \|\sqrt{M}(Lp' - \delta)\|^2 + \|\sqrt{W}(Cp' - h)\|^2, \quad (6)$$

where L is the matrix form of the Laplacian operator, C encapsulates the barycentric coordinates, $\delta$ is a vector with the x, y or z coordinates of Laplacian $\delta_i$, h is a vector containing the respective handle coordinates, M and W are diagonal matrices containing the weights $A_i$ and $w_i$, respectively, and $p'$ is the vector with the deformed vertex coordinates. The deformed tooth template can be reconstructed by a minimization in the linear least square sense.

The global deformation energy can be reformulated to:

$$E(p') = p'^T(L^TML + C^TWC)p' - 2p'^T(L^TM\delta + C^TWh) + \delta^T M\delta + h^T Wh. \quad (7)$$

The minimization $$\frac{\partial}{\partial p'} E(p') = 0 \quad (8)$$

leads to the normal equations $$(L^TML + C^TWC)p' = L^TM\delta + C^TWh \quad (9)$$

which are basically a linear system of size n×n.

For the Laplacian surface deformation of the tooth template 7 the handle weights $\text{handlew}_{g,I,p,D}(i,d,\alpha)$ may be defined by the following formula:

$$\text{handlew}_{g,I,p,D}(i,d,\alpha) = \text{globalw}_{g,I,p}(i) \cdot \text{distw}(i,d)_{D,I} \cdot \text{anglew}(\alpha). \quad (10)$$

The global weighting function 19 may be defined by $$\text{globalw}_{g,I,p}(i) = g \cdot \left(\frac{i}{I}\right)^p, \quad (11)$$

wherein $g \geq 1$ is a global weighting factor, $I \geq 1$ is the number of iteration steps, $i \in [1,I]$ is the current iteration step and the power $p \geq 1$ determines the shape of the function.

Figure 7:
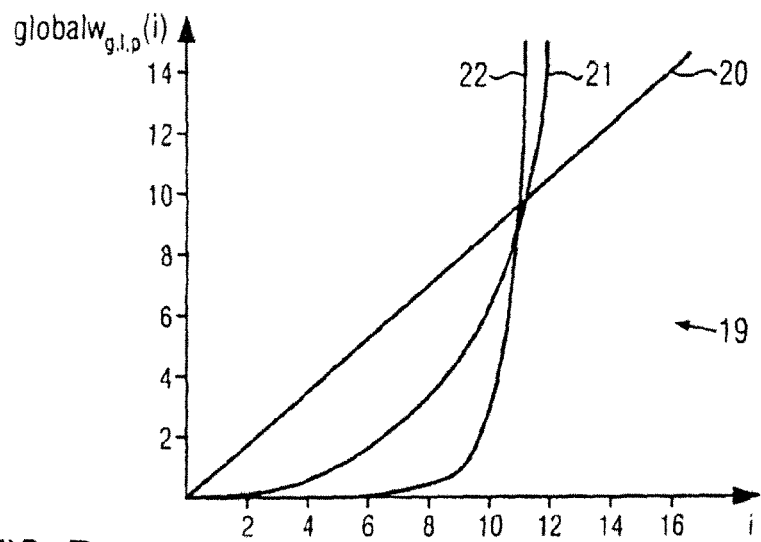
FIG. 7 shows the global weighting function.

In FIG. 7 three exemplary curves 20, 21, 22 of the global weighting function 19 are shown, wherein for all three curves the global weighting factor g and the number of iteration steps I are the same, respectively. The line 20 represents the global weighting function 19 having a power of p=1. The other two curves 21, 22 have larger power values.

Figure 9:
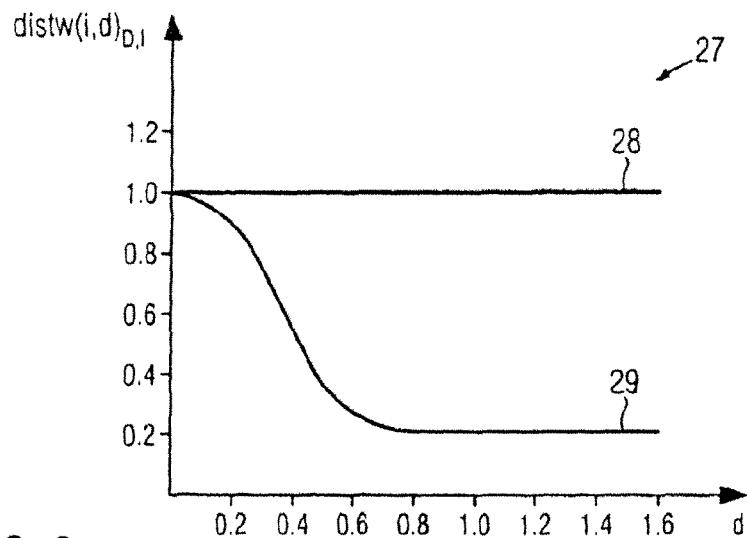
FIG. 9 shows distance weighting function.

To define the distance weighting function 27 as shown in FIG. 9, the Wendland weighting function 23 may be taken into account and thus, the distance weighting function may be defined by $$\text{distw}(i, d)_{D,I} = 1 - \text{wendland}_{4,I}(I - i) + \begin{cases} 0 & \text{for } d \geq D \\ \text{wendland}_{4,I}(I - i) \cdot \text{wendland}_{4,D}(d) & \text{else}' \end{cases} \quad (12a)$$

or preferably by $$\text{distw}(i, d)_{D,j} = \text{wendland}_{8,I}(i) + \begin{cases} 0 & \text{for } d \geq D \\ (1 - \text{wendland}_{8,I}(i)) \cdot \text{wendland}_{4,D}(d) & \text{else}' \end{cases} \quad (12b)$$

wherein $d \geq 0$ is the distance, $D \geq 0$ is the support.

Figure 8:
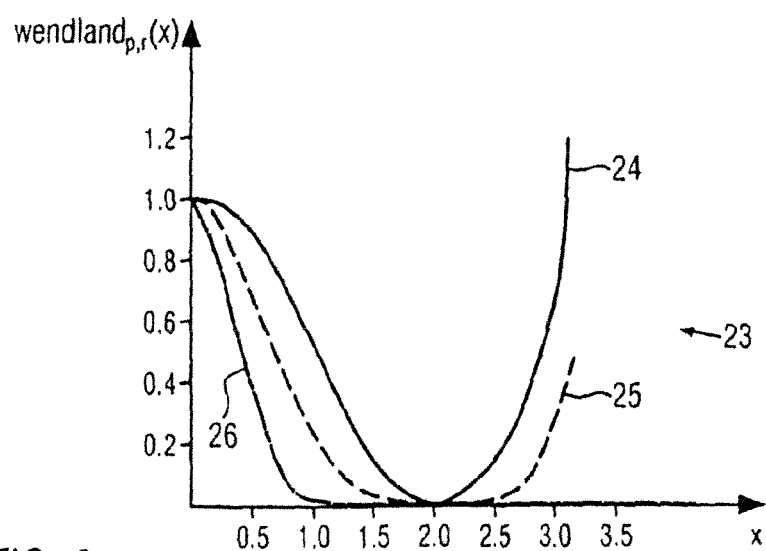
FIG. 8 shows the Wendland weighting function.

The Wendland weighting function 23 is defined by $$\text{wendland}_{p,r}(x) = \left(1 - \frac{x}{r}\right)^p \cdot \left(\frac{p \cdot x}{r} + 1\right) \quad (13)$$

wherein $r \geq 0$ is the radius of support and $p \geq 2$ determines the shape of the function. In FIG. 8, three exemplary Wendland weighting functions 24, 25, 26 are shown that all have the same radius of support r. The parameter p increases for the curve with the solid line 24 to the dashed line 25 and to the dot and dash line 26.

In FIG. 9, two curves for the distance weighting function 27 are shown. Both curves have the same number of iterations I and the same support D, respectively. For the first iteration i=1 the curve 28 of the distance weighting function 27 shows almost no dependency from the distance d. As the iteration process proceeds, i.e. at a larger iteration step i, the distance weight for larger distances between target and handle decreases as can be seen in FIG. 9. This behaviour of the distance weighting function 27 reduces the impact of false projections for large distances between target and handle.

Figure 10:
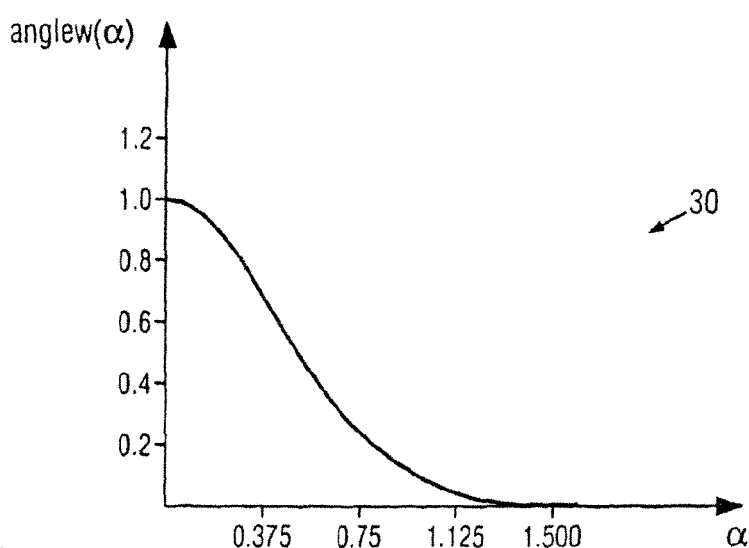
FIG. 10 shows the angle weighting function.

The angle weighting function 30 may be defined by the following formula:

$$\text{anglew}(\alpha) = \begin{cases} 0 & \text{for } \alpha \geq \pi/2 \\ \text{wendland}_{4,\pi/2}(\alpha) & \text{else}' \end{cases} \quad (14)$$

wherein $\alpha \in [0,\pi]$ may be the angle between the normal direction of the target and the normal direction of the handle. In FIG. 10 an exemplary curve of the angle weighting function 30 is shown.

FIGS. 11a and 11b show how the distance 33 between a target 12 and a handle 11 may be defined. The surface of the rest tooth 1 and the tooth template 7 are shown as being represented by triangular meshes 31, 32, respectively. Also other polygonal meshes are possible for describing the surface of the rest tooth 1 and/or the tooth template 7, wherein the type of polygons do not have to be the same for both meshes but may be the same.

As shown in FIG. 11a, the target 12 is a vertex on the surface of the rest tooth 1, while the handle on the tooth template 7 is a point inside a triangle of the mesh 32. FIG. 11b shows an enhanced view of FIG. 11a to better illustrate an exemplary definition of the angle $\alpha$ 36 between the normal direction of the target 12 and the normal direction 35 of the handle 11. In the depicted case, a line for determining the handle 11 on the tooth template 7 is given by going through the target 12 on the surface of the rest tooth 1 and being directed along the normal direction 34 at the target 12. The line 33 may also extend from the target 12 to the handle 11 in another direction then the normal direction 34.

After applying a fixed number of iterations i, a tooth template 7 may exist that has been deformed such that it describes the unprepared regions of the rest tooth 1. This part of the tooth template 7 that lies inside the preparation margin 4, i.e. the area that is surrounded by the preparation margin, may describe the surface of the dental restoration to be designed, wherein this surface represents the surface of the dental restoration that will not be hidden by the rest tooth 1 after attaching the dental restoration to the rest tooth 1. This surface may be e.g. a part of the chewing surface of a molar.

For the final design of the dental restoration the part of the tooth template 7 inside the preparation margin is relevant. To extract this part, the so-called deformed tooth template 18, from the tooth template 7, a digital cut along the preparation margin 4 may be performed, such that only data being related to the tooth template 7 inside of the preparation margin 4 is taken into account for further processes.

Figure 5:
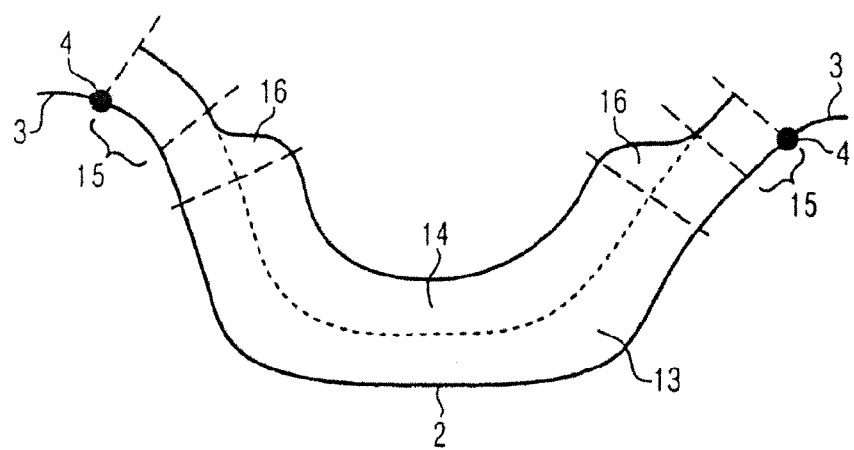
FIG. 5 shows cement gap and spacer gap.

After finalizing the deformation of the tooth template 7, the surface of the dental restoration describing the lower surface 2 may be adapted by adding a cement gap 13 and a spacer gap 14, wherein a at some distance 15 from the preparation margin 4 a spacer transition 16 may exist as shown in FIG. 5. For example, an offset function may be chosen to achieve a smooth transition from the cement gap 13 to the spacer gap 14:

$$\mathit{offset}_{b,t,c,s}(d) = c + \begin{cases} 0 & \text{for } d \leq b \\ s & \text{for } d \geq b+t \\ \frac{s}{2}\cdot\left(1+\sin\left(\pi\cdot\frac{d-b}{t}-\frac{\pi}{2}\right)\right) & \text{else,} \end{cases} \quad (15)$$

wherein d is the geodesic distance to the preparation margin 4, b is the distance of the spacer gap 14 to the preparation margin 4, t is the spacer gap transition 16, c is the thickness of the cement gap 13 and s is the thickness of the spacer gap 14.

Figure 6:
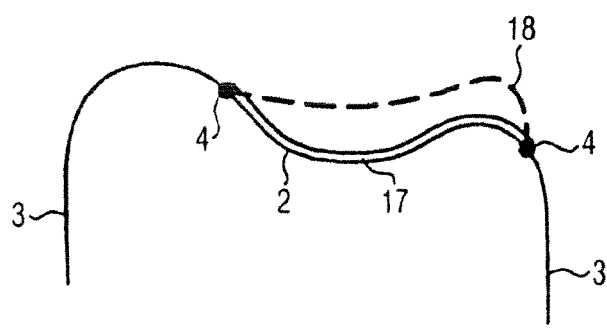
FIG. 6 shows prepared tooth, deformed tooth template and minimal surface.

For the manufacturing of the dental restoration it is required that a certain minimum wall thickness is ensured. Therefore, a minimal surface 17, as shown in FIG. 6, may be constructed and every vertex of the deformed tooth template 18 may be required to lie above this minimal surface 17. The minimal surface 17 may be constructed by an offset on the rest tooth 1 and the mesh of the cavity to be provided with the dental restoration.

To correct the deformed tooth template 18 with respect to the minimal surface 17, rays (i.e. lines) may be cast from vertices of the deformed tooth template 18 along the positive normal direction of the respective vertex. A vertex is below the minimum wall thickness if the ray belonging to said vertex intersects a mesh triangle of the minimal surface and the difference between the normal direction of the vertex and the normal direction of the triangle is less than $\pi/2$. In such a case, a respective handle is selected and the intersection point on the minimum surface 17 is selected as target. Handle weights may be set in the same manner as for the deformation process of the tooth template 7, but the distance weighting is described independent from the current iteration as no general positioning is required.

In order to achieve a good correction result, first the deformation may be applied to the boundary of the deformed tooth template 18 while fixing handles in the interior using large handle weights. In a second deformation step, the boundary may be fixed and the interior may be adjusted to the minimal surface 17.

One exemplary for an offset to define the minimal surface is given by $$o_{b,w,W}(d) = \begin{cases} 0 & \text{for } d \leq 0 \\ b\sqrt{1-\left(1-\frac{d}{b}\right)^2} & \text{for } d > 0, d \leq b \\ w & \text{for } d \geq W \\ b+\frac{w-b}{2}\cdot\left(1+\sin\left(\pi\cdot\frac{d-b}{W-b}-\frac{\pi}{2}\right)\right) & \text{else,} \end{cases} \quad (16)$$

wherein b>0 is a predefined wall thickness at the boundary and w>b a predefined wall thickness at a geodesic distance W>b from the boundary. This function guarantees a minimum wall thickness b at the boundary and ensures that deformed tooth template 18 forms at least almost a rectangular angle at the preparation margin 4 with respect to the lower surface 2 of rest tooth 1.

Depending on the shape of the transition between the lower surface 2 and the unprepared part of the rest tooth 1, the thickening near the preparation margin 4 may have different forms. In case, the transition forms almost a rectangular angle, then almost no or none thickening can be observed and a flat and smooth transition between the corrected, deformed tooth template (i.e. the deformed tooth template 18 that has been corrected taking into account a minimal thickness) and the unprepared part of the rest tooth 1 is provided. In case, the transition has an angle smaller than 90°, then a thickening may be provided ensuring that the dental restoration will have a sufficient thickness also near the preparation margin.

Another possibility for defining a minimal surface 17 is to apply an offset along the normal direction of each vertex of the lower surface 2 (wherein preferably the cement gap 13 and/or spacer gap 14 has already been added to the lower surface 2). Such an offset may have a predefined value over the whole range of the lower surface 2 or the offset may have smaller values near the preparation margin 4 and larger values at some predefined distance from the preparation margin 4 or vice versa. Instead of taking into account the normal direction of each vertex, an average of several normal directions of several vertices may be determined and then an offset may be applied to this averaged normal direction.

The invention claimed is:

1. Computer-implemented method for digitally designing a dental restoration for a rest tooth using a tooth template, wherein the rest tooth is described by scanned data of the rest tooth or a dental model of the rest tooth, and the tooth template is described by data of the tooth template, and wherein a normal direction to a surface at a point is the same as a normal direction to a tangent plane to the surface at the point, the method comprising the steps of:
   generating, via a processor, for display on a computer display, data sets for the rest tooth and tooth template depicted as objects;
   automatically deforming, via the processor, the tooth template towards the surface of the rest tooth by Laplacian surface deformation using an angle weighting function depending on:
   the angle between the normal direction of a target on the surface of the rest tooth or the normal direction of a handle on the tooth template; and
   the direction of a line connecting the target and the handle;

wherein the angle weighting function is used to weight the handle for deforming the tooth template towards the rest tooth; and defining the data of the tooth templates as a first polygonal mesh describing a surface of the tooth template and defining the data of the rest tooth as a second polygonal mesh describing the surface of the rest tooth, wherein the handle lies inside, on an edge or on a vertex of a polygon of the first polygonal mesh, and wherein the target lies inside, on an edge or on a vertex of a polygon of the second polygonal mesh.

2. The computer-implemented method according to claim 1, wherein the method further comprises defining the line connecting the target and the handle as being directed along:
the normal direction of the target, or
the normal direction of the handle.

3. The computer-implemented method according to claim 1, wherein the method further comprises defining the line connecting the target and the handle as being directed along the normal direction of the target and the angle weighting function is depending on the normal direction of the handle on the tooth template and the direction of the line connecting the target and the handle.

4. The computer-implemented method according to claim 1, wherein the method further comprises defining the angle weighting function as decreasing with increasing angle.

5. The computer-implemented method according to claim 4, wherein the decrease of the angle weighting function is described by a Wendland weighting function.

6. The computer-implemented method according to claim 1, wherein the method uses a product of the angle weighting function and at least one or two of a global weighting function or a distance weighting function to weight the handle for deforming the tooth template towards the rest tooth.

7. The computer-implemented method according to claim 6, wherein the method further comprises defining the global weighting function as increasing with each iteration step in case the Laplacian surface deformation is performed iteratively.

8. The computer-implemented method according to claim 6 or 7, wherein the method further comprises defining the distance weighting function as decreasing with increasing distances between the target and the handle, wherein the dependence of the distancing weighting function on the distance varies with each iteration step when the Laplacian surface deformation is performed iteratively.

9. The computer-implemented method according to claim to 1, wherein the method further comprises :
a) when the target lies within a polygon of the second polygonal mesh, selecting the normal direction of the target by the normal direction of the polygon of the second polygonal mesh or by an average of the normal direction of the polygon of the second polygonal mesh and the normal directions of its neighboring polygons, or
b) when the handle lies within a polygon of the first polygonal mesh, selecting the normal direction of the handle by the normal direction of the polygon of the first polygonal mesh or by an average of the normal direction of the polygon of the first polygonal mesh and the normal directions of its neighboring polygons; or
c) when the target lies on an edge of a polygon of the second polygonal mesh, selecting the normal direction of the target by the normal directions of polygons having this edge; or
d) when the handle lies on an edge of a polygon of the first polygonal mesh, selecting the normal direction of the handle by the normal directions of polygons having this edge; or
e) when the target lies on a vertex of a polygon of the second polygonal mesh, selecting the normal direction of the target by an average of the normal directions of polygons that have this vertex as a corner point or of polygons that lie within a sphere or a volume of a predefined size around the vertex, or
f) when the handle lies on a vertex of a polygon of the first polygonal mesh, selecting the normal direction of the handle by an average of the normal directions of polygons having this vertex as a corner point or of polygons that lie within a sphere or a volume of a predefined size around the vertex.

10. Computer-implemented method according to claim 1, wherein the step of automatically deforming comprises
automatically deforming the tooth template by means of Laplacian surface deformation such that a prepared part of the rest tooth, within a preparation margin, is covered by a portion of the tooth template, and
firstly choosing a point on the surface of the rest tooth or dental model of the rest tooth as a target of the Laplacian surface deformation and then, based on the chosen target, choosing a point on the tooth template as a handle.

11. The computer-implemented method of claim 10, wherein the point is selected on the preparation margin.

12. Non-transitory computer-readable medium having stored thereon instructions, which when executed by a processor, performs a method for digitally designing a dental restoration for a rest tooth using a tooth template, wherein the rest tooth is described by scanned data of the rest tooth or a dental model of the rest tooth, and the tooth template is described by data of the tooth template, and wherein a normal direction to a surface at a point is the same as a normal direction to a tangent plane to the surface at the point, the method comprising the steps of;
generating, via a processor, for display on a computer display, data sets for the rest tooth and tooth template depicted as objects;
automatically deforming, via the processor, the tooth template towards the surface of the rest tooth by Laplacian surface deformation using an angle weighing function depending on;
the angle between the normal direction on a target on the surface of the rest tooth or the normal direction of a handle on the tooth template; and
the direction of a line connecting the target and the handle;
wherein the angle weighting function is used to weight the handle for deforming the tooth template towards the rest tooth; and
defining the data of the tooth template as a first polygonal mesh describing a surface of the tooth template and defining the data of the rest tooth as a second polygonal mesh describing the surface of the rest tooth, wherein the handle lies inside, on an edge or on a vortex of a polygon of the first polygonal mesh, and wherein the target lies inside, on an edge or on a vertex of a polygon of the second polygonal mesh.

* * * * *